United States Patent [19]

Hancock

[11] Patent Number: 4,484,822
[45] Date of Patent: Nov. 27, 1984

[54] METHOD AND APPARATUS FOR DETERMINING BOILING POINTS OF LIQUIDS

[76] Inventor: Robert D. Hancock, 475 Lakeshore Dr., Chrystal Bay Cove, Unit 32, Incline Village, Nev. 89450

[21] Appl. No.: 326,274

[22] Filed: Dec. 1, 1981

[51] Int. Cl.³ ............................................ G01K 17/00
[52] U.S. Cl. ......................................... 374/27; 374/16
[58] Field of Search ....................... 374/27, 16, 28, 24, 374/182; 73/64.2, 61.3, 302; 136/227, 230, 217, 226, 222

[56] References Cited

U.S. PATENT DOCUMENTS

| | | | |
|---|---|---|---|
| 2,314,877 | 3/1943 | Hall | 136/222 |
| 3,260,113 | 7/1966 | Benson et al. | 136/222 |
| 3,446,056 | 5/1969 | Koch | 374/27 |
| 3,690,177 | 9/1972 | Fluegel | 374/182 |
| 3,698,236 | 10/1972 | Markey | 374/27 |
| 3,813,925 | 6/1974 | Fenske et al. | 73/64.2 |
| 3,992,229 | 11/1976 | Hall, Jr. | 136/222 |
| 4,250,739 | 2/1981 | Audeh et al. | 374/27 |
| 4,348,117 | 9/1982 | Michels | 374/27 |

OTHER PUBLICATIONS

Andrews, D. H. and Kokes, R. J., *Fundamental Chemistry*, N.Y., John Wylie & Sons, 1963, pp. 296–297.
Moore, W. J., *Physical Chemistry*, Englewood Cliffs, N.J., Prentice Hall, 1962, p. 106
Cole, R., "Homogenous and Heterogenous Nucleation", In: Van Stralen, S. and Cole, R., *Boiling Phenomena*, N.Y., McGraw-Hill, 1979, vol. I, pp. 71–73.

*Primary Examiner*—Charles Frankfort
*Assistant Examiner*—David R. Schuster
*Attorney, Agent, or Firm*—Fitch, Even, Tabin & Flannery

[57] ABSTRACT

A liquid sample is placed in a closed vessel. A thermocouple junction is submerged in the liquid sample. The pressure of the liquid is decreased, or the thermocouple junction is heated, until boiling from the thermocouple junction is detected. The pressure or temperature is then varied until the boiling just ceases. The pressure and temperature at cessation of boiling define the boiling point free of spurious liquid superheating effects.

6 Claims, 10 Drawing Figures

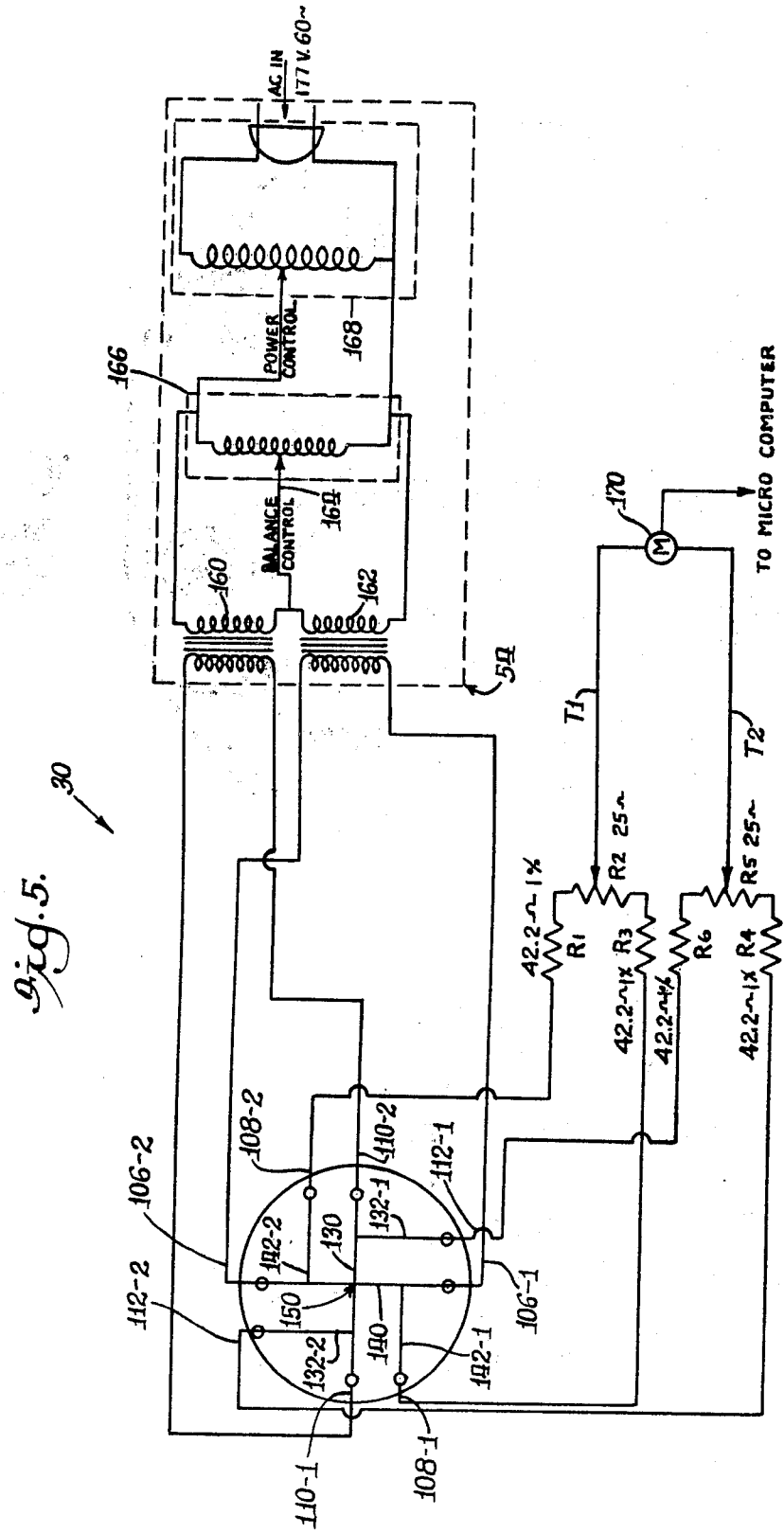

METHOD AND APPARATUS FOR DETERMINING BOILING POINTS OF LIQUIDS

The subject matter of this application is related to that of a concurrently executed and filed United States application entitled Ebulliometric Hot Spot Detector, filed Dec. 1, 1981 as Ser. No. 326,224.

BACKGROUND OF THE INVENTION

This invention relates generally to measuring and testing apparatus. More particularly, this invention relates to an ebulliometric technique for the determination of boiling points of liquids.

The boiling temperature of a liquid substance may be defined, as for example, in Andrews, D. H. and Kokes, R. J., *Fundamental Chemistry*, New York, John Wylie and Sons, 1963, p. 296, as the temperature where the pressure of the vapor phase of the substance is equal to the external pressure upon the liquid phase at the same temperature. The relationship between pressure and temperature at the boiling point of the substance, or more precisely on the boiling curve on a pressure-temperature diagram for the substance, may be determined by measuring the vapor pressure as a function of the temperature of the liquid. A prior art method for carrying out such a measurement is described in Moore, W. J., *Physical Chemistry*, Englewood Cliffs, N.J., Prentice-Hall, 1962, p. 106.

Moore discusses the use of an isoteniscope, shown schematically in FIG. 1. A bulb 1 and an attached short U-tube 2 are filled with a liquid sample to be studied. The bulb and U-tube are contained in a thermostat 3 having a thermometer 4 for measuring the temperature in the thermostat. Pressure means 5 may be provided for varying the pressure on the arm of the U-tube 2 external to the bulb 1. A manometer 6 measures the applied pressure on the external arm of the U-tube 2. The liquid is allowed to boil vigorously until all air is removed from the sample side of the U-tube 2. The temperature of the thermostat 3 is then varied over the range of temperatures at which the boiling point is to be determined, and the pressure applied by the pressure means 5 are adjusted until the arms of the U-tube contain the same height of liquid. The pressure and temperature as measured by the manometer 6 and the thermometer 16 are then recorded as a point on the pressure versus temperature boiling curve of the sample.

A difficulty with the isoteniscope method is related to the fact that there is a range of temperatures, at a given pressure, in which the vapor and liquid phases may simultaneously exist because of supersaturation and superheating phenomena. As illustrated in FIG. 2, taken from Cole, R., "Homogeneous and Heterogeneous Nucleation," in: Van Stralen, S., and Cole, R., *Boiling Phenomena*, (New York, McGraw-Hill, 1979), p. 71, boiling is characterized by an envelope rather than by a single curve on a pressure versus specific volume (or, equivalently, temperature) diagram. At any given pressure below the critical point there is a range of specific volumes of the fluid and vapor phases possible for the system. Fluid between the dashed line passing through the point C and the solid line passing through the point B may exist in a metastable superheated state, and vapor to the right of the dashed line passing through the point E and the solid line passing through the point F may exist in a metastable supersaturated state. A liquid-vapor mixture in the thermodynamic region between the two dashed lines would be mechanically unstable.

In the isoteniscope method the determination of vapor pressure is complicated by the fact that the vapor on the sample side of the U-tube may be supersaturated if the measurements of vapor pressure are made after cooling. On the other hand, if measurements are made after heating of the sample from a lower temperature then the liquid may be superheated. In either case, the relationship between pressure and temperature will not be accurately given, thereby leading to inaccurate determination of the boiling point curve.

The problem in the isoteniscope method is illustrative of problems in prior art methods of determining boiling points where bulk measurements are made on material with both the liquid and vapor phases present. When the equilibrium point at which the measurement is to be made is approached from a lower temperature, then the liquid will generally be superheated. When the equilibrium point is approached from a higher temperature, then the vapor will generally be supersaturated.

A second difficulty with prior art methods involving bulk fluid phase and gas phase materials simultaneously present is that bulky and complicated apparatus are needed, and such methods do not lend themselves easily to automation.

SUMMARY OF THE INVENTION

The present invention relates to a method and apparatus for the determination of boiling points of liquids by introduction of a hot spot thermocouple which is heated to cause boiling at a point location in the liquid and then cooled to determine the temperature and pressure at which boiling terminates. The termination temperature and pressure define the boiling point on a pressure versus temperature diagram. The method does not require bulk vapor and bulk liquid in equilibrium with each other, and, therefore, supersaturated vapor is not appreciably present to affect the boiling point determination. On the other hand, because the hot spot is cooled to the point where boiling ceases, liquid superheating effects are minimized. Because the method focuses upon the detection of boiling or bubbling in a liquid, it may be termed "ebulliometric."

A specific construction of the hot spot thermocouple will include a pair of fine thermocouple wires, one of iron and one of constantan, for example, crossed and welded at a point. Bimetallic systems other than iron-constantan may also be used within the scope of the present invention. Alternating current is applied to the wires to heat each wire and, especially, to heat the point of welding, which becomes the hot spot.

Each of the wires may be tapped on either side of the hot spot and the two tap on each wire connected through a respective potentiometer. Taps of the two potentiometers may be adjusted to have the same AC potential. The voltage difference between the two taps is then just the DC output of the thermocouple.

The thermocouple wires are made very fine, partly to minimize heating power requirements needed to replace heat loss from the wires to the surrounding fluid. Reduction of the wire diameters lessens the surface area the wires present to the surrounding fluid for heat conduction. Furthermore, heat conduction from the wires to the fluid leads to convective motion of the fluid surrounding the wires thereby obscuring precise viewing of boiling sites in the fluid. Also, large wires are more likely to have small imperfections capable of acting as boiling sites, whereas it is desirable to have only the welded hot spot as a boiling site at temperatures close to the boiling point.

Fine thermocouple wires are difficult to handle. Accordingly, a specific construction of the hot spot thermocouple may comprise a non-conductive body having a flat surface and eight passages leading to the surface. Each passage securely holds an insulated wire lead, each lead made from one of the two kinds of wire used in the thermocouple hot spot. The two kinds of fine thermocouple wire are disposed upon the flat surface and each joined, respectively, to four wire leads of the same kind of wire. The resulting figure on the flat surface resembles a whirligig and may be descriptively referred to as such.

Welding of the wires disposed upon the body's flat surface is greatly simplified by use of a welding fixture including a table with micrometer movement. Welding may conveniently be done with a split electrode welding head viewed under a microscope.

A preferred embodiment of the invention incorporates microprocessor control. The presence of boiling may conveniently be determined by acoustic means, optical means, capacitance means (since the presence of vapor bubbles changes the dielectric constant of the medium), or other means not specifically described herein. Thus, very generally, an ebulliometric measurement system for determining boiling points of liquids may comprise a container means for containing a liquid under pressure, a hot spot thermocouple heatable over a range of temperatures, the thermocouple elements being used to measure the hot spot temperature, and bubble detection means to determine the onset and cessation of boiling as the hot spot is heated and then cooled. A microprocessor may be used to automate the control of pressure in the container and at each one of a predetermined set of pressures to record the temperature at which boiling ceases.

It is accordingly an object of the present invention to provide for the determination of boiling points of liquids using an ebulliometric method suitable for use with a microprocessor. It is also an object of the present invention to provide a method and apparatus for determination of liquid boiling points that minimize spurious effects due to superheating of liquid or supersaturation of vapor. These and other objects, features, and advantages of the invention will be apparent from the following description of the specific construction of a preferred embodiment as illustrated in the accompanying drawings.

DESCRIPTION OF THE DRAWINGS

FIG. 5 is a circuit diagram of electrical circuitry associated with the whirligig hot spot thermocouple shown in FIG. 4A;

DETAILED DESCRIPTION OF THE SPECIFIC CONSTRUCTION AND OPERATION OF A PREFERRED EMBODIMENT

System Construction

Figure 1:
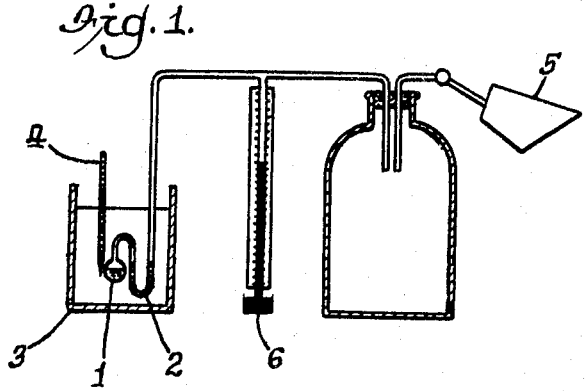
FIG. 1 is a schematic representation of a prior art isoteniscope apparatus used for boiling point determinations.
Figure 2:
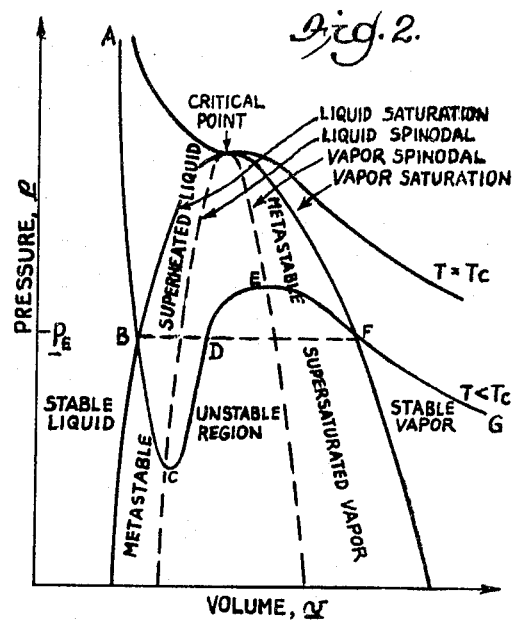
FIG. 2 shows the relationship between pressure p and specific volume v for liquid-vapor phases of a material in thermodynamic equilibrium.
Figure 3:
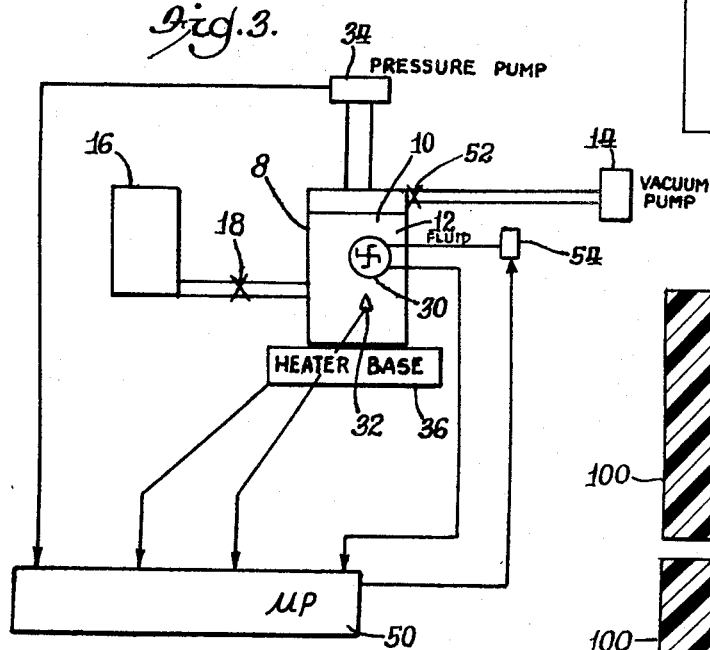
FIG. 3 is a diagrammatic illustration of a specific construction of a preferred embodiment of an ebulliometric measurement system for determining boiling points of liquids in accordance with the present invention.

As illustrated in FIG. 3, a vessel 8 capable of withstanding pressure forms a chamber 10 that is filled with a liquid sample 12 for which the boiling point curve is to be determined. The bubble cauldron described in the concurrently filed application could provide a suitable chamber. A vacuum pump 14 may be used to evacuate the chamber 10 prior to filling it from a liquid reservoir 16 through a valve 18 in order to avoid dissolved atmospheric gases in the liquid sample 12. A whirligig hot spot thermocouple 30 is disposed within the chamber 10, and a small bubble detection transducer 32 is placed in the vicinity of the whirligig hot spot thermocouple 30. The chamber 10 may be connected to a pressure pump 34 for varying the pressure in the chamber. The pressure pump 34 may be similar to one disclosed in the concurrently filed application. The chamber 10 may be placed upon a heatable and coolable base 36 used for controlling the ambient temperature of the liquid sample 12 in the container 10. The pressure pump 34, heater and cooler base 36, transducer 32, and whirligig hot spot thermocouple 30 all provide inputs to a microprocessor 50.

Figure 4B:
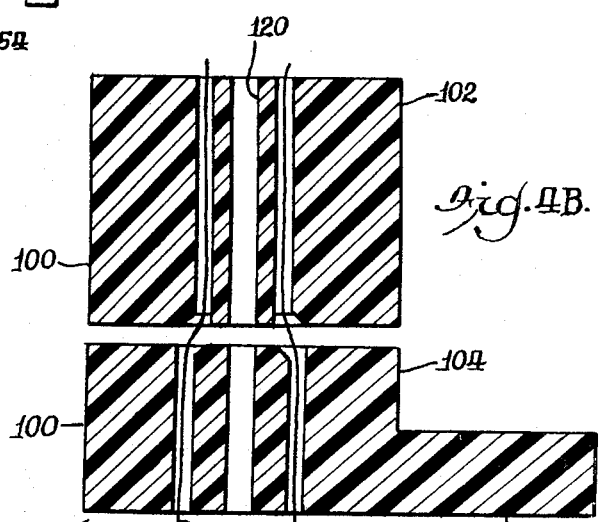
FIG. 4B is a sectional view of the whirligig hot spot detector shown in FIG. 4A, taken along line B—B.
Figure 4A:
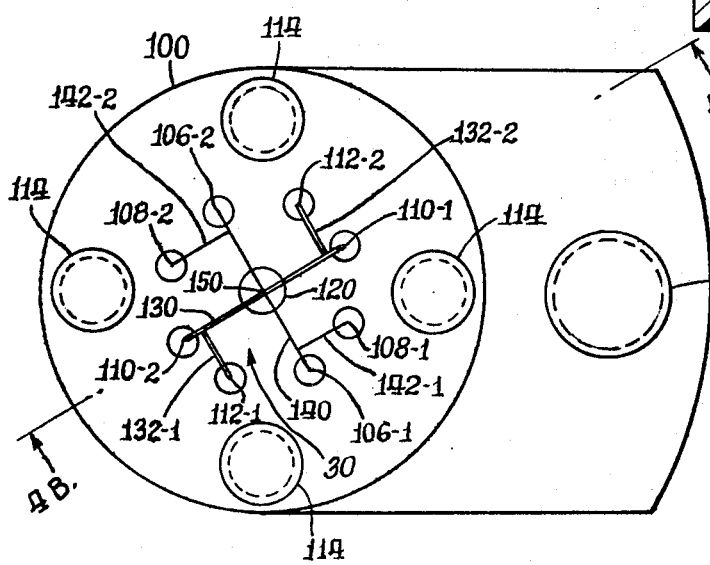
FIG. 4A is a plan view of a whirligig hot spot thermocouple shown as a block in FIG. 3.

FIGS. 4A and B illustrate a preferred construction of the whirligig hot spot thermocouple 30. A non-conducting body 100, which may be made of plastic and comprised of an upper section 102 and a lower section 104, provides for holding securely four pairs of insulated lead wires 106-1, 106-2, 108-1, 108-2, 110-1, 110-2, 112-1 and 112-2 as shown in the FIGS. 4A and B. The lead wires 106, 108, 110, 112 may be held securely by providing passages from the top face of the upper portion 102 through the upper portion and through the lower portion 104, the passages in the upper portion 102 and lower portion 104 being displaced from each other when the portions are joined together as shown particularly in FIG. 4B. The portions may be held together by four screws 114 and the lower portion may be provided with a flange 116 tapped for securing to another surface by a screw 118. In a particular construction the lead wires 110 and 112 are iron, and the lead wires 106 and 108 are constantan. Lead wires 106, 108, 110, and 112 having 0.01" diameter were used in the particular construction described herein. The body 100 may also be drilled through the upper and lower portion in a direction parallel to the passage of the eight lead wires with a hole 120, with the passages containing the lead wires disposed symmetrically on the circumference of a circle concentrically surrounding the hole 120, as shown in FIG. 4A. A substantially straight piece of iron thermocouple wire 130 is disposed upon the smooth upper face of the upper body 102 across the approximate center of the hole 120 and connecting the lead wires 110-1 and 110-2. The lead wires 110-1 and 110-2 are also both made of iron in order to avoid dissimilar metal junctions with the thermocouple wire 130. The two lead wires 110 are welded to the thermocouple wire 130, as will be described. A pair of iron tap wires 132-1 and 132-2 are welded to a second pair of iron lead wires 112-1 and 112-2, respectively, which are disposed next to the pair of wires 110. The lead wires 112-1 and 112-2 are approximately oppositely located across the face of the upper section 102 with respect to the hole 120. The iron tap wires 132 are welded to the thermocouple wire 130 at approximately equal distances from the center of the hole 120, thereby tapping the thermocouple wire 130. The wires 110 are the iron heater wires, and the wires 112 are the iron sensing wires.

A fine substantially straight piece of constantan thermocouple wire 140 is disposed on the upper face of the upper body 102 at substantially right angles to the iron thermocouple wire 130. The constantan thermocouple wire 140 is welded to the pair of wires 106, which are constantan heater wires, in the same manner that the iron thermocouple wire 130 is welded to the iron heater wires 110. A pair of constantan tap wires 142-1 and 142-2 tap the constantan thermocouple wire 140 and are welded to the lead wires 108 which are also of constantan, thereby making a construction of constantan wire similar to and at substantially right angles with respect to the construction of iron wire. The iron and constantan thermocouple wires 130 and 140 are welded together at the approximate center of the hole 120, thereby forming a junction or hot spot 150.

The iron sensing wires 112-1 and 112-2 connect, respectively, to a pair of resistors R6 and R4 as illustrated in FIG. 5. The two resistors R6, R4 are then connected by a potentiometer R5. The constantan sensing wires 108-1 and 108-2 are similarly connected to a pair of resistors R3 and R1 which in turn are connected by a potentiometer R2. The connections of the sensing wires 108, 112 to the resistors R1, R3, R4, R6 comprise the thermocouple reference junction. The potentiometers R2 and R5 are tapped respectively by taps T1 and T2 which together comprise the output terminals of a thermocouple sensing circuit. The resistors R1, R3, R4, and R6 all have substantially the same resistance and are maintained at substantially the same temperature, which may be measured independently.

The heater leads 106 and 110 are respectively connected to the secondary terminals of a pair of filament transformers 162 and 160, also as illustrated in FIG. 5. The primaries of the filament transformers 160, 162 are connected together and the common connection connected to a tap 164 of a variable ratio transformer 166. The other terminals of the primaries of the filament transformers 160 and 162 connect to the output terminals of the transformer 166. The transformer 166 is then connected to an adjustable power source 168 as indicated symbolically in FIG. 5. The pair of filament transformers 160 and 162, together with the transformer 166 and the adjustable power source 168, thereby comprise a power supply 54.

Persons familiar with electrical circuits will appreciate that the taps T1 and T2 may be adjusted so that there is zero AC voltage between them. As a result, the voltage between the taps T1 and T2 will be substantially only the DC output voltage produced by the whirligig hot spot thermocouple 30. This DC output voltage may be measured by a voltmeter means 170 and the result transmitted to the microprocessor 50. The resistances of the portions of the iron thermocouple wire 130 between the hot spot 150 and the respective connections of the iron sensing wires 112-1 and 112-2 in combination with the resistances of the resistors R6 and R4 and respective portions of the potentiometer R5 form a resistance bridge that can be balanced by adjustment of the tap T2. This adjustment puts the tap T2 at the AC potential of the hot spot 150. Similarly, the resistances of the portions of the constantan thermocouple wire 140 between the respective connections of the constantan sensing wres 108-1 and 108-2 in combination with the resistances of the resistors R3 and R1 and respective portions of the potentiometer R2 form a resistance bridge that can be balanced by adjustment of the tap T1. This adjustment puts the tap T1 also at the AC potential of the hot spot 150. Hence, this balance puts the taps T1 and T2 at the same AC potential, irrespective of the AC voltages applied to the respective thermocouple wires 130, 140.

Figure 6B:
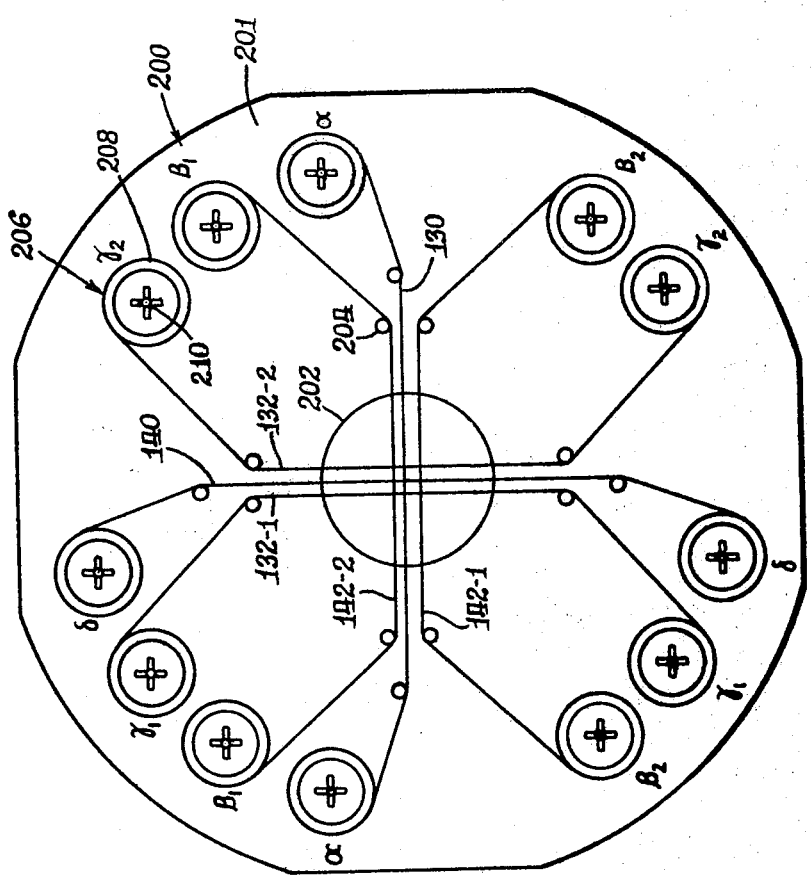
FIGS. 6A and 6B are isometric and detail plan views of a wire setup and holding fixture used in construction of the whirligig hot spot thermocouple shown in FIGS. 4A and 4B.
Figure 6A:
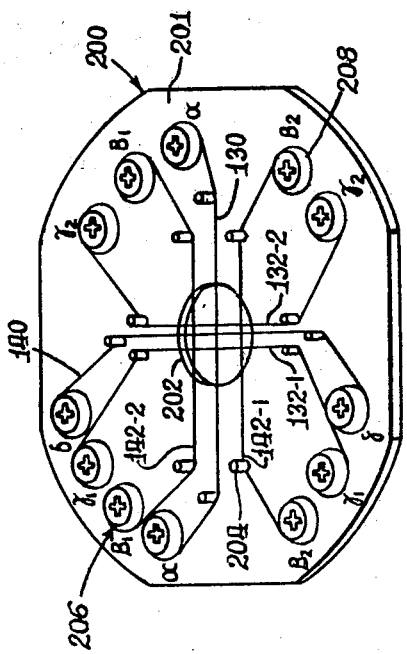

The fine wires 130, 132, 140, and 142 were of 0.001" diameter in the specific construction described herein. Welding of such fine wires is difficult. As a result, it is desirable to have special equipment for assembling the whirligig hot spot thermocouple 30. FIG. 6A and FIG. 6B illustrates a specific construction of a wire setup and holding fixture 200 for facilitating the handling of extremely fine wire such as the thermocouple junction wires 130, 140 and tap wires 132, 142. The fixture 200 comprises an approximately circular metal plate 201, which may be made of brass, having an access hole 202 in the approximate center. Triplets of positioning pins such as pin 204 are arranged in triangles at approximately 90° intervals about the access hole, the apexes of the triangles being directed to the outer circumference of the plate 200. Twelve hold-downs such as hold-down 206 are arranged about the circumference of the plate 200. Each hold-down 206 comprises an O-ring 208 held in place by a screw 210, the screw being adjustable to force the O-ring against the surface of the plate 201. Wire may be held in place on the surface of the brass plate 201 by being drawn between a pair of pins such as the pin 204 and a pair of hold-downs such as the hold-down 206 so as to be held in place under tension across the access hole 202. The wires are strung with two triplets of wires at right angles to each other. In one direction an iron thermocouple wire 130 is strung between and parallel to a pair of constantan tap wires 142, whereas in the orthogonal direction a constantan thermocouple wire 140 is strung between a pair of iron tap wires 132.

Figure 7:
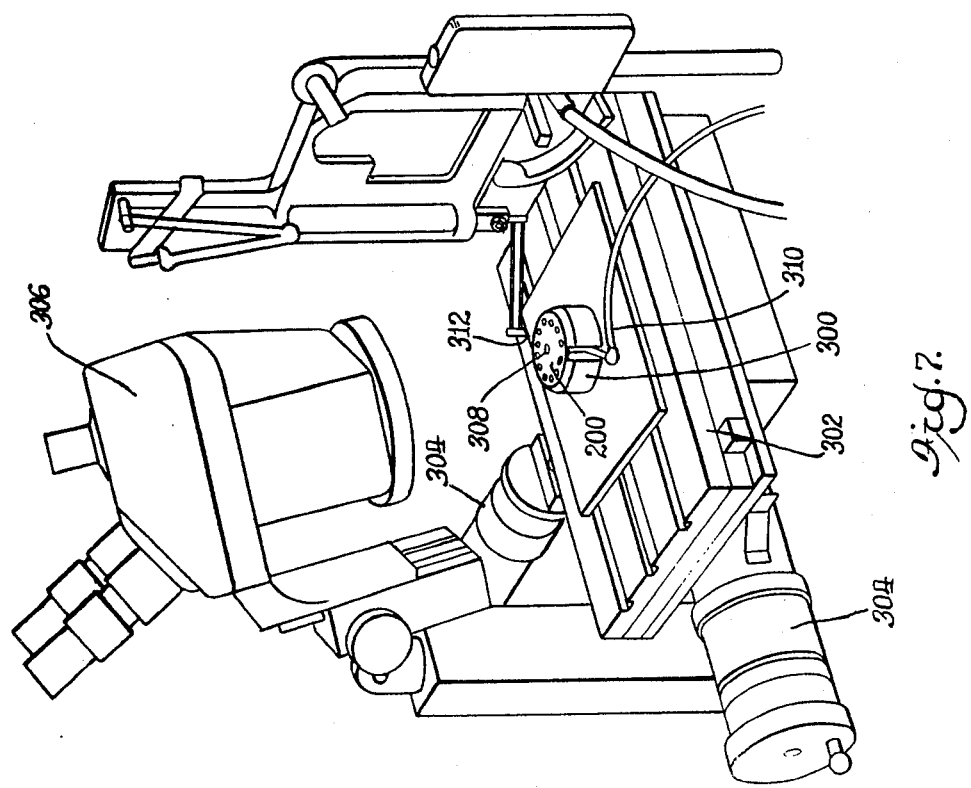
FIG. 7 is an isometric view of a welding fixture used to hold the setup and holding fixture shown in FIGS. 6A and 6B during construction of the whirligig hot spot thermocouple.

The fixture 200, when loaded with wire, is then placed in a welding fixture 300 as illustrated in FIG. 7. The welding fixture 300 comprises a cylindrical body providing a seat for the fixture 200 accessible from above, and may be affixed by any convenient means to a micrometer table 302 having micrometer controls 304 disposed under a microscope 306. The welding fixture 300 includes a copper rod 308 that fits from below into the central access hole 202 of the fixture 200 to provide a lower welding electrode substantially flush with the upper face of the brass plate 201. A power cable 310 may be connected to the central rod 308.

An upper electrode 312 with a fine point tip may conveniently be positioned by a foot pedal and the power controlled by suitable means such as a hand switch.

The iron and constantan thermocouple wires 130, 140 cross in the approximate center of the fixture as shown in FIG. 6B. The crossing point may be positioned under the upper electrode by means of micrometer table adjustments and the thermocouple wires 130, 140 then welded together by lowering the upper electrode onto the junction point and applying voltage. In the construction described herein the upper electrode 312 is applied to the junction point of the thermocouple wires 130, 140 with a force of 15 grams and a voltage of between 0.570 and 0.640 AC rms volts applied between the upper and lower electrodes 312, 308. The iron tap wires 132-1 and 132-2 are similarly welded to the iron thermocouple wire 130 and the constantan tap wires 142-1, 142-2 welded to the constantan thermocouple wire 140. Fifteen grams of force are applied for each weld, and the voltages applied to the electrodes 310, 308 are between 0.450 and 0.500 volts for the constantan-on-constantan welds and between 0.690 and 0.740 volts for the iron-on-iron welds.

Figure 8:
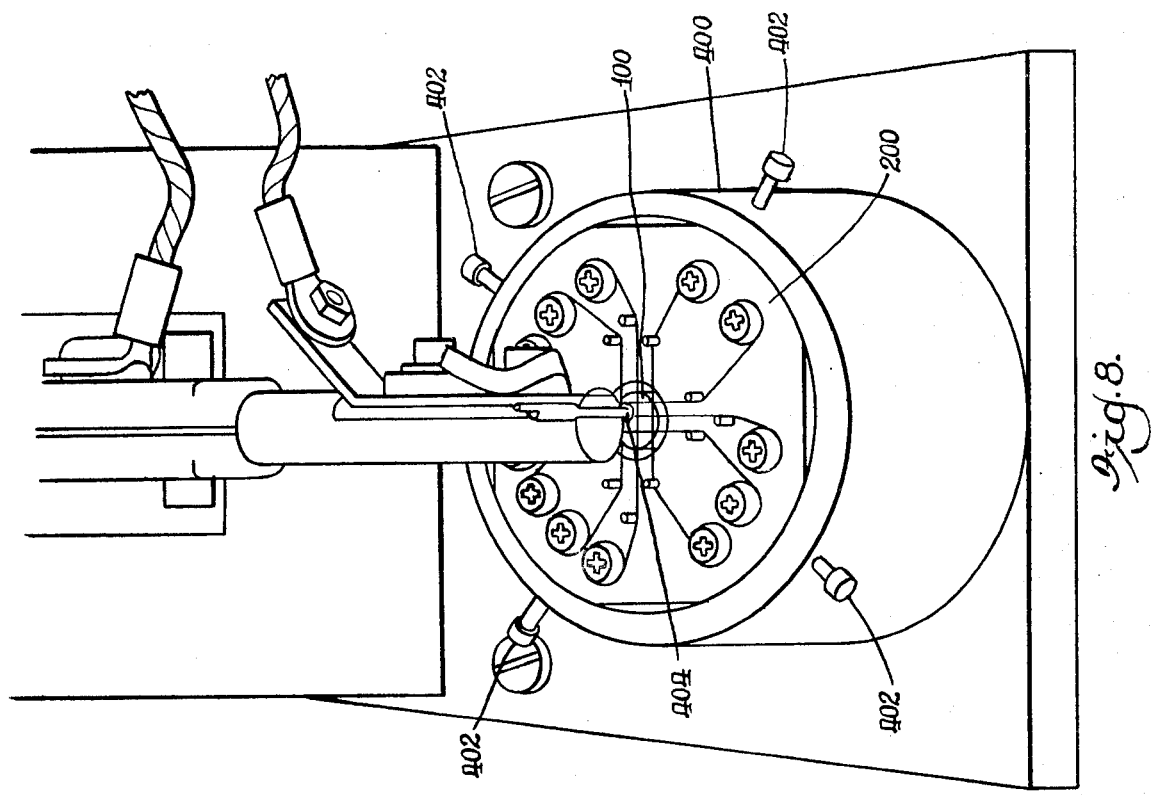
FIG. 8 is an isometric view of a transfer fixture used to hold the setup and holding fixture shown in FIGS. 6A and 6B during construction of the whirligig hot spot thermocouple.

The fixture 200 is next placed in a transfer fixture 400 shown in the isometric view in FIG. 8. The transfer fixture 400 also comprises a cylindrical body providing a seat for the fixture 200 accessible from above. The transfer fixture 400 provides means to support the upper face of the non-conducting body 100 within the central hole 202 of the fixture 200. The support for the non-conducting body 100 is provided to position the central hole 120 in the upper face of the non-conducting body 100 underneath the welded intersection of the thermocouple wires 130, 140 with the leads 106, 108, 110, 112 substantially in contact with the wires of the same kind on the face of the fixture 200. Four centering screws 402 may be provided in the transfer welding fixture 400 to position the fixture 200 with respect to the non-conducting body 100. A double electrode welding head 404 having an electrode spacing of approximately 0.003" may be used to weld the thermocouple wires 130, 140 and taps 132, 142, respectively, to the lead wires 110, 106, 112, 108. The welds may be made applying 30 grams of force and between 1.160 & 1.210 AC rms volts. Excess wire may be trimmed by application of the double electrode welding head 404 against the wire backed either by plastic or air. When the backing is plastic or air, the wires become very hot and melt because heat cannot be conducted away from the wires. Conversely, it is necessary when welding that the wires being welded be in contact with a sufficiently massive heat conductor.

System Operation

For operation of the system, the sample liquid to be tested is placed in the reservoir 16. The chamber 10 is evacuated by the vacuum pump 14 and then isolated from the vacuum pump by closing a valve 52. The valve 18 is next opened to fill the container 10 from the reservoir 16. The heatable and coolable base 36 is controlled to provide a predetermined ambient temperature in the fluid 12, which temperature may be read out by operation of the microprocessor 50 from the whirligig hot spot thermocouple 30. The pressure may also be controlled to a predetermined value through operation of the pressure pump 34 under the control of the microprocessor 50.

The microprocessor 50 then activates the power supply 54 of the whirligig hot spot thermocouple 30 to raise the temperature of the hot spot 150 until bubbling is detected by the transducer 32 and the detection signal transmitted to the microprocessor 50. After commencement of bubbling, the microprocessor 50 causes the power supplied to the hot spot 150 to be reduced until detection of bubbling by the transducer 32 just ceases. The hot spot 150 temperature and liquid pressure when cessation of boiling occurs then correspond to one point on the boiling curve of the sample material. The process may be repeated at a sequence of preselected pressures programmed into the microprocessor 50 to determine a boiling point curve for the sample.

It will, of course, be understood that modification of the present invention in its various aspects would be apparent to those skilled in the art, some being apparent only after study and others being a matter of routine design. For example, the particular arrangement of components shown in FIG. 3 is not a necessary feature of the invention. Various other arrangements could be found suitable for containment of a liquid sample and for applying pressure to such liquid. Microprocessor control, as indicated herein, while convenient, is also not a necessary feature of the invention. With certain detection means other than acoustic it may be desirable to run the system manually for precision determination of boiling points. Persons skilled in the art will conceive of other forms and arrangements of components which will also serve the purpose of boiling point determination. As such, the scope of the invention should not be limited by the particular embodiment and specific construction described herein but should be defined only by the appended claims and equivalents thereof.

What is claimed is:

1. An ebulliometric measurement system for measuring boiling points of liquids comprising:
    vessel means for statically containing a liquid at determined pressure,
    heating means for selectively heating a predetermined spot within said liquid contained in said vessel to determined temperature above the ambient temperature of said liquid surrounding said spot,
    control means for controlling at least one of said pressure and temperature to cause bubbling to occur substantially exclusively from said spot and thereafter to stop said bubbling, and
    means for signaling the pressure in said liquid and the temperature of said spot substantially coincident with the cessation of said bubbling.

2. An ebulliometric measurement system for measuring boiling points of liquids comprising:
    vessel means for statically containing a liquid under pressure,
    heating means for locally heating a predetermined spot within said liquid to a temperature above the ambient temperature of said liquid surrounding said spot sufficient to cause boiling in said liquid substantially exclusively at said spot within said vessel means when said pressure is sufficiently low,
    control means for decreasing said pressure on said liquid untill bubble formation commences substantially exclusively from said spot upon boiling of said liquid thereat and then increasing said pressure until cessation of bubble formation occurs, and means for determining the temperature of said spot and the pressure in said liquid at which the cessation of bubble formation occurs.

3. An ebulliometric measurement system for determining the boiling points of liquids comprising:

vessel means for statically containing a liquid under pressure, heating means for selectively heating a predetermined spot within said liquid contained in said vessel to a temperature above the ambient temperature of said liquid surrounding said spot, control means for controlling at least one of (1) the pressure of said liquid contained in said vessel and (2) the temperature of said spot to cause bubbling in said liquid substantially exclusively from said spot and thereafter to stop said bubbling, bubble detection means responsive to said bubbling for producing a bubble cessation signal upon cessation of said bubbling, temperature sensing means for providing a temperature signal systematically related to said temperature of said spot, pressure sensing means for providing a pressure signal systematically related to said pressure of said liquid, and indicating means responsive to said bubble cessation signal, said temperature signal and said pressure signal for indicating said temperature and pressure at substantially the cessation of bubbling.

4. A method for measuring boiling points of liquids comprising the steps of:

statically containing and confining a liquid, selectively heating a predetermined spot within said liquid above the ambient temperature of said liquid surrounding said spot, varying one of (1) pressure in the liquid and (2) temperature of said spot to cause said liquid to bubble substantially exclusively from said spot, further varying one of (1) the pressure in the liquid and (2) the temperature of said spot to cause said bubbling to cease, and determining the pressure of said liquid and the temperature of said spot at substantially the cessation of said bubbling.

5. A method for measuring boiling points of liquids according to claim 4 wherein said bubbling and cessation of bubbling is caused by varying the pressure on said liquid.

6. A method for measuring the boiling points of liquids according to claim 4 wherein said bubbling and cessation of bubbling is caused by varying the temperature at said predetermined spot.

* * * * *